(12) United States Patent
Greenleaf et al.

(10) Patent No.: US 7,234,460 B2
(45) Date of Patent: Jun. 26, 2007

(54) METERING VALVE FOR A METERED DOSE INHALER PROVIDING CONSISTENT DELIVERY

(75) Inventors: David J. Greenleaf, Loughborough (GB); Peter D. Hodson, Breaston (GB); Graham R. Purkins, Loughborough (GB); Gary D. Mahon, Wilford (GB); Heinz G. Klein, Bonn (DE)

(73) Assignee: 3M Innovative Properties Company, St. Paul, MN (US)

( * ) Notice: Subject to any disclaimer, the term of this patent is extended or adjusted under 35 U.S.C. 154(b) by 818 days.

(21) Appl. No.: 10/655,196

(22) Filed: Sep. 4, 2003

(65) Prior Publication Data

US 2004/0139965 A1    Jul. 22, 2004

Related U.S. Application Data

(60) Provisional application No. 60/408,637, filed on Sep. 6, 2002.

(30) Foreign Application Priority Data

Jul. 7, 2003    (GB)    ................... 0315791.4

(51) Int. Cl.
   *B65B 1/04*    (2006.01)
(52) U.S. Cl. ............... 128/200.23; 222/402.2; 222/402.24; 239/350
(58) Field of Classification Search ........... 128/200.23, 128/200.14, 200.18, 200.21; 222/402.1, 222/402.16, 402.2, 402.24, 402.25; 239/350
See application file for complete search history.

(56) References Cited

U.S. PATENT DOCUMENTS

| | | | |
|---|---|---|---|
| 1,800,156 A | 4/1931 | Rotheim | |
| 1,892,750 A | 1/1933 | Rotheim | |
| 2,723,055 A | 11/1955 | Beard, Jr. | .................... 222/394 |
| 3,123,261 A | 3/1964 | Gorman | |
| 3,385,482 A | 5/1968 | Frangos | .................... 222/402.2 |
| 3,405,846 A | 10/1968 | Klun | |
| 3,592,357 A | 7/1971 | Welch | ........................ 222/193 |
| 3,727,806 A * | 4/1973 | Wilmot | ................... 222/402.2 |
| 3,741,446 A | 6/1973 | Marand | ....................... 222/402 |
| 4,362,257 A * | 12/1982 | Shay | ........................ 222/402.2 |
| 4,427,137 A | 1/1984 | Dubini | .................... 222/402.2 |
| 4,798,226 A | 1/1989 | Struth | ...................... 137/512.4 |
| 4,819,834 A | 4/1989 | Thiel | .......................... 222/355 |
| 4,858,790 A | 8/1989 | Howlett | ................... 222/402.2 |
| 4,953,759 A | 9/1990 | Schmidt | .................. 222/402.2 |

(Continued)

FOREIGN PATENT DOCUMENTS

EP    0 061 973 B1    10/1982

(Continued)

*Primary Examiner*—Steven O. Douglas
(74) *Attorney, Agent, or Firm*—Ted K. Ringsred

(57) ABSTRACT

The present invention relates to a novel design for a metering valve that provides improved consistency of formulation delivery. Generally, the metering valve includes (a) a valve stem that generally defines a longitudinal axis and includes a body portion having a metering surface, wherein the longitudinal axis and a plane tangential to at least a portion of the metering surface define an angle from about 2° to about 90°; and (b) a valve body having an internal chamber defined at least in part by the body wall and includes a metering portion configured to substantially conform to the metering surface of the valve stem.

35 Claims, 10 Drawing Sheets

U.S. PATENT DOCUMENTS

| | | | |
|---|---|---|---|
| 5,085,351 A | 2/1992 | Martin | 222/287 |
| 5,169,038 A | 12/1992 | Di Giovanni | 222/402.2 |
| 5,400,920 A | 3/1995 | Barnhart | 222/1 |
| 5,477,992 A | 12/1995 | Jinks et al. | 222/402.2 |
| 5,484,088 A | 1/1996 | Martin | 222/402.2 |
| 5,703,187 A | 12/1997 | Timmers | 526/282 |
| 5,772,085 A | 6/1998 | Bryant et al. | 222/402.2 |
| 5,938,085 A | 8/1999 | Conroy et al. | 222/402.2 |
| 5,983,927 A | 11/1999 | Simon et al. | 137/516 |
| 6,112,950 A | 9/2000 | Di Giovanni et al. | 222/402.1 |
| 6,123,237 A | 9/2000 | Lasserre et al. | 222/402 |
| 2004/0139966 A1 | 7/2004 | Hodson | 128/200 |

FOREIGN PATENT DOCUMENTS

| | | |
|---|---|---|
| EP | 0 567 348 B1 | 10/1993 |
| EP | 0 801 009 B1 | 10/1997 |
| FR | 1.225.163 | 6/1960 |
| FR | 1.461.685 | 2/1966 |
| GB | 1035304 | 7/1966 |
| GB | 1 201 918 | 8/1970 |
| GB | 1 524 293 | 9/1978 |
| GB | 2 004 526 A | 4/1979 |
| GB | 2 086 845 A | 5/1982 |
| GB | 2 206 100 A | 12/1988 |
| WO | WO 92/11190 | 7/1992 |
| WO | WO 93/22221 | 11/1993 |
| WO | WO 95/03984 | 2/1995 |
| WO | WO 99/20664 | 4/1999 |
| WO | WO 03/000570 A1 | 1/2003 |

* cited by examiner

METERING VALVE FOR A METERED DOSE INHALER PROVIDING CONSISTENT DELIVERY

CROSS-REFERENCE TO RELATED APPLICATION

This application claims priority to U.S. Provisional Patent Application No. 60/408,637, filed Sep. 6, 2002 and GB Patent Application No. 0315791.4, filed Jul. 7, 2003.

BACKGROUND

Metering valves are a common means by which aerosols are dispensed from aerosol containers. Metering valves are particularly useful for administering medicinal formulations that include a liquefied gas propellant and are delivered to a patient in an aerosol.

When administering medicinal formulations, a dose of formulation sufficient to produce the desired physiological response is delivered to the patient. The proper predetermined amount of the formulation must be dispensed to the patient in each successive dose. Thus, any dispensing system must be able to dispense doses of the medicinal formulation accurately and reliably to help assure the safety and efficacy of the treatment.

Metering valves have been developed to provide control over the dispensing of medicinal aerosol formulations. A metering valve may be used to regulate the volume of a medicinal formulation passing from a container to a metering chamber, which defines the maximum amount of the formulation that will be dispensed as the next dose. Reliable and controllable flow of the medicinal formulation into the metering chamber may contribute to the accuracy and/or precision of the metering of successive doses of the formulation. Thus, reliable and controllable flow of the medicinal formulation into the metering chamber may improve performance of the metering valve and, therefore, may be highly desirable.

In some metering valves, the metering chamber fills with the medicinal formulation prior to the patient actuating the valve stem and thereby releasing the dose. The metering chamber is refilled with formulation after dispensing one dose so that the metering valve is ready to discharge the next dose. Consequently, the metering chamber contains formulation at all times except for the brief time during which the valve stem is depressed by the user to discharge a dose. Also, the passageways through which the formulation must flow to reach the metering chamber are often narrow and tortuous. As a result, metering valves configured in this way have a number of disadvantages resulting in, for example, erratic dosing due to loss of prime. "Loss of prime" means the occurrence of vapor or air voids in the metered volume, thereby leading to a shortfall in the volume of dose being metered by the valve. A principal cause of loss of prime is the presence of restrictions in the entry passageway or passageways through which formulation must pass to fill the metering chamber. Such restrictions can lead to flow disruption and thus also to the occurrence of vapor or air voids in the metering chamber.

Another phenomenon that can lead to erratic dosing is loss of dose. "Loss of dose" means a change in the amount of suspended drug or excipient particles in a metered dose of formulation, compared to the average composition of the bulk formulation in the container. A principal cause of loss of dose is the settling of drug particles into, or their movement out of, restricted regions of the metering valve such that the proper concentration of formulation cannot subsequently be obtained within the restricted regions prior to dose delivery. For example, drug particles may settle in a residual metering volume—any part of the metering valve bounded by a metering surface and that, when the metering valve is in the resting position, remains fluid filled but is not in substantially free-flowing communication with the bulk formulation.

In other metering valves, residual metering volume may be limited to some extent by designing the metering valve so that the metering chamber does not materialize unless and until the valve stem is actuated. However, even in these metering valves, a small residual metering volume exists when the metering valve is at rest because a small annular gap exists between the valve stem and the metering valve body.

Actuation of these valve stems can be divided into a filling stage and a discharge stage. The filling stage begins as the valve stem is depressed during actuation. The action of depressing the valve stem causes the formation of a transient metering chamber, which is in fluid communication with the residual metering volume defined by the small annular gap. As the valve stem is depressed, the transient portion of the metering chamber expands and formulation enters the metering chamber. As displacement of the valve stem continues, a stage is reached at which filling of the transient metering chamber stops.

Eventually, displacement of the valve stem continues to the discharge stage, in which the metered formulation is discharged. In these valves, a single actuation thus causes rapid filling of the transient metering chamber followed by discharge of the formulation to the patient. Generally, metered formulation does not reside for any appreciable length of time in the metering chamber in these metering valves. However, some formulation may reside in the residual metering volume defined by the small annular gap when the metering valve is at rest.

Some metering valves limit the height of the annular gap, thereby reducing the residual volume and limiting the amount of formulation that resides in the metering chamber between actuation events.

While a metering valve having a transient metering chamber provides advantages over other types of metering valves for the delivery of aerosol formulations, the flow of formulation from the container to the metering chamber may be disrupted. Disrupted flow of formulation refers to filling a metering chamber through one or more bottleneck regions of significantly restricted access. Flow through the bottleneck regions may be impeded sufficiently to give rise to substantially incomplete filling of the metering chamber, particularly under conditions typical of patient use. When this happens, formulation may be delivered in inconsistent or inaccurate doses. Of course, all metering chamber inlets become significantly restricted immediately prior to being sealed off during actuation. Disrupted flow, as just described, refers to flow access during the majority of the filling stage of actuation.

Certain metering valves have been designed to improve the flow of formulation into the metering chamber. For example, some metering valves include angled spillway filling channels designed to limit disruption of the flow of formulation into the metering chamber. Less disrupted flow may decrease the likelihood and extent to which vapor or air voids form in the metered volume and, therefore improve performance of the metering valve.

SUMMARY OF THE INVENTION

The present invention relates to a novel design for a metering valve that provides improved consistency of formulation delivery. The metering valve of the present invention includes a valve stem designed to (1) limit or eliminate the residual metering volume, thereby reducing the amount of formulation that resides in the metering chamber while the metering valve is at rest, and (2) limit restrictions on the free flow of formulation into the metering chamber. Consequently, consistent delivery of formulation is obtained by reducing the effects of loss of prime and loss of dose.

The present invention provides an aerosol metering valve that includes a valve body and a valve stem that generally defines a longitudinal axis and comprises a metering gasket configured to be able to form a transient, substantially fluid-tight seal between the valve stem and a sealing portion of the valve body. The valve stem includes a body portion including a metering surface, wherein the longitudinal axis and a plane tangential to at least a portion of the metering surface define an angle from about 2° to about 90°.

In another aspect, the present invention provides an aerosol metering valve including (a) a valve body that includes a diaphragm having walls that define an aperture; (b) a metering stem that generally defines a central axis and also partially defines an interior space, the metering stem including a sealing portion, an inlet recess distal to the sealing portion, a metering surface distal to the inlet recess, and a discharge gasket distal to the metering surface, wherein the central axis and a plane tangential to at least a portion of the metering surface defines an angle from about 2° to about 90°; (c) a valve stem in slidable, sealing engagement with the aperture and including: (1) a sealing portion across a portion of the interior space from the inlet recess of the metering stem; said sealing portion comprising a metering gasket configured to be able to form a transient fluid-tight sliding seal with at least a portion of the metering stem sealing portion, (2) a metering surface configured to substantially conform to the metering surface of the metering stem, (3) an interior surface, (4) a discharge recess in a portion of the interior surface.

DETAILED DESCRIPTION OF THE INVENTION

The following description is set forth in terms of an aerosol metering valve used to dispense an aerosol formulation from an aerosol container. However, the metering valve and methods of the present invention have application to virtually any pressurized fluid requiring delivery of an accurate, metered dose. In particular, the metering valves described herein are useful for dispensing medicinal aerosol formulations.

When used to dispense medicinal aerosol formulations, a metering valve according to the present invention may be used to administer virtually any aerosol formulation of drug into a body cavity of a patient, such as the mouth, nose, anus, vagina, ears, or onto the eyes or any skin area of the patient. However, the present invention is not limited to medicinal applications and may be used wherever a precise amount of material from a pressurized fluid is to be delivered to a given region.

Figure 1:
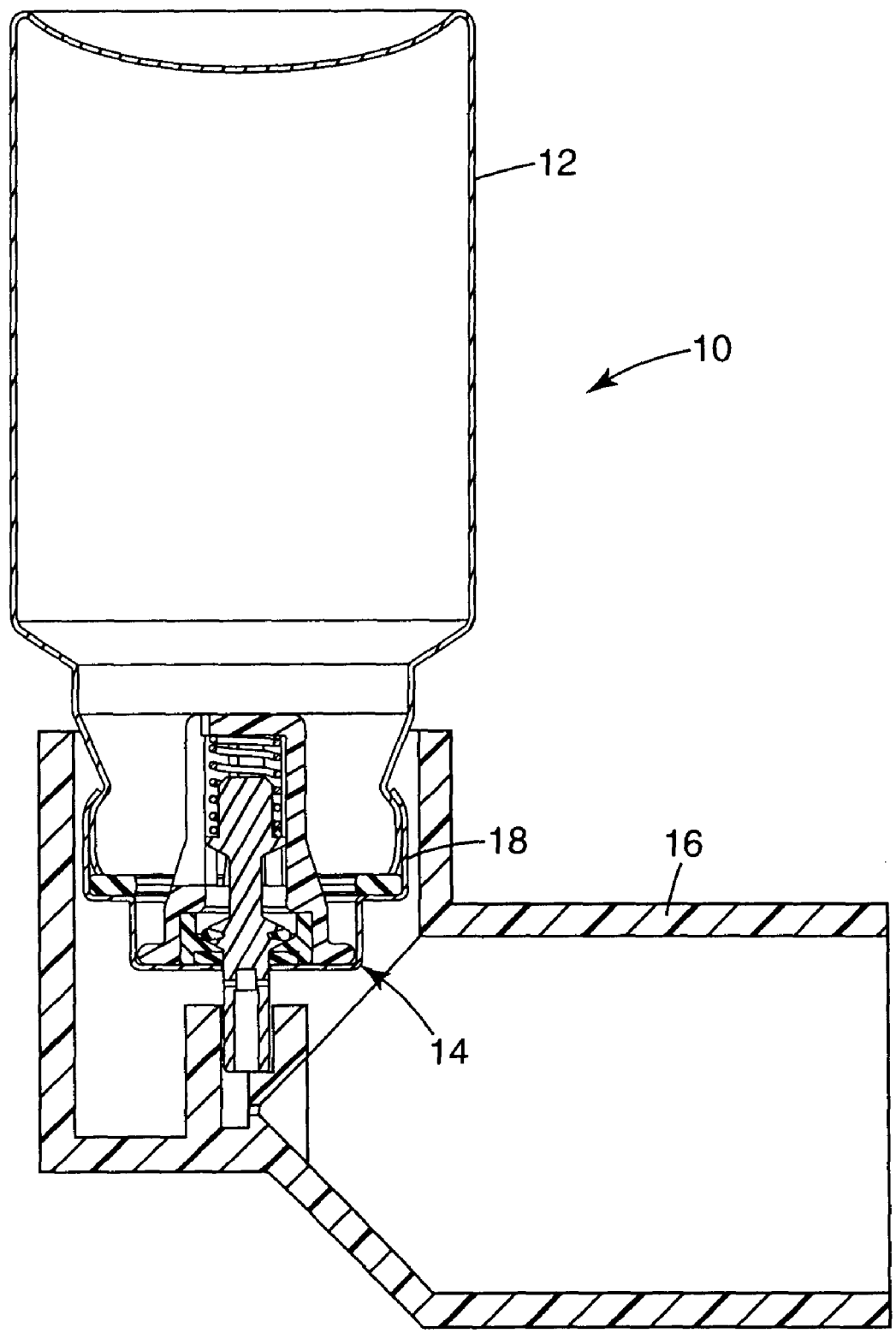
FIG. 1 is a cross-sectional view of a metered dose inhaler including an embodiment of the aerosol metering valve according to the present invention.

FIG. 1 shows an aerosol dispensing apparatus, generally designated as 10, that incorporates one embodiment of a metering valve 14 according to the present invention. The top end of the metering valve 14 is crimped around the end of a conventional aerosol container 12, while a conventional discharge piece 16 is mounted around the bottom of the metering valve 14. Thus, aerosol formulation is dispensed downwardly from the aerosol container 12, through the metering valve 14, then through the discharge piece 16 where it is delivered to a patient. The discharge piece 16 directs the aerosol formulation toward the body cavity or skin area to which the formulation is to be delivered. For example, discharge piece 16 may be a mouthpiece that can be inserted into the patient's mouth, thereby providing oral administration of the aerosol formulation.

The aerosol-dispensing device shown in FIG. 1 is merely one example of how a metering valve according to the present invention can be incorporated into a dispensing apparatus. Furthermore, the configuration of the discharge piece 16 depends upon the application for the aerosol.

In many of the figures, a metering valve or valve stem is shown in isolation for ease of illustration. The valve stems shown in isolation may be combined with one or more additional components to form a metering valve. Such metering valves, as well as metering valves shown in isolation in the figures, may be combined with one or more additional components to form an aerosol dispensing device. It is understood that any particular feature shown in a metering valve and/or valve stem embodiment may be combined with features shown in other embodiments and/or incorporated appropriately within other embodiments.

Figure 2:
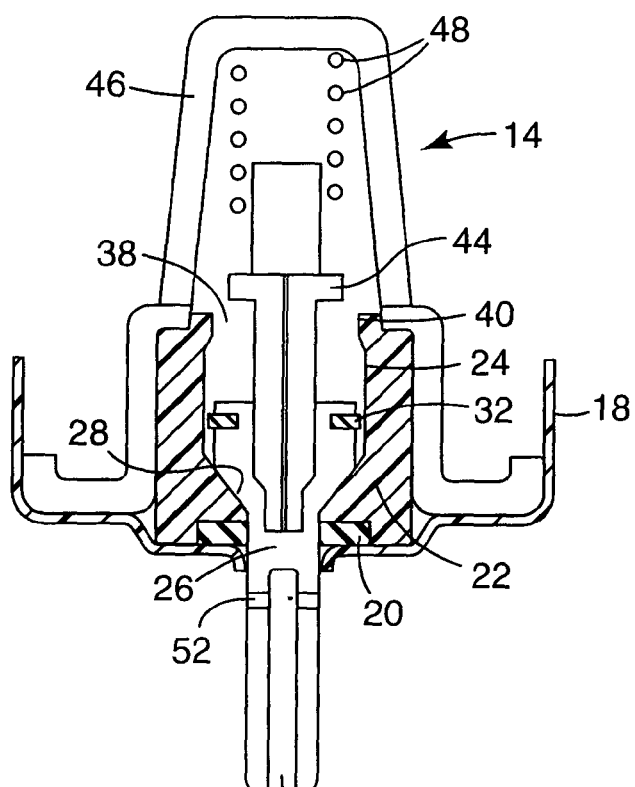
FIG. 2 is an enlarged cross-sectional view of an embodiment of another aerosol metering valve according to the present invention in the resting position.

Referring to FIG. 2 showing an embodiment of a metering valve 14 (in the resting position), the metering valve 14 typically includes a housing 18 that serves to house the various components of the metering valve 14. The top portion of the housing 18 attaches to the aerosol container 12 (as shown in FIG. 1). A valve body 22, typically seated within the valve housing 18, in turn provides a housing for a valve stem 26. The valve body 22 includes an interior surface 24 defining an internal chamber or cavity of the valve body.

The metering valve 14 typically includes a spring cage 46 that, together with the valve body 22, defines an interior chamber 38, a portion of which is occupied by a portion of the valve stem 26. One or more inlets (not shown) provide open and unrestricted fluid communication between the interior chamber 38 and the aerosol container 12.

The valve stem 26 includes two portions, a body portion and a stem portion. The stem portion includes that portion of the valve stem that is outside the valve housing 18 when the valve stem 26 is in the resting position shown in FIG. 2. During actuation of the valve stem 26, however, the stem portion will be displaced inwardly with respect to the metering valve 14, as described more fully below, so that some of the stem portion will be transiently positioned inside the valve housing 18. The stem portion includes a passageway 50 through which a metered dose of formulation is discharged, as will be described more fully below. The passageway includes one or more side holes 52.

The body portion of the valve stem 26 is that portion that is positioned within the valve housing 18 throughout actuation of the valve stem 26. The body portion of the valve stem 26 includes a metering surface 28 and a sealing surface 30.

The body portion of the valve stem 26 is configured to have substantially the same shape as the surrounding wall of the valve body 22. Thus, as can be seen in the embodiment shown in FIG. 2, a substantial portion of the metering surface 28 of valve stem 26 rests in contact with the interior surface of the valve body 24 when the metering valve is in the resting position, thereby minimizing the annular gap between the valve stem and valve body when the metering valve is in the resting position, and thus minimizing residual metering volume.

The metering valve may include a spring guide 44 mounted on the end of the valve stem body portion opposite the stem portion and a spring 48 within the interior chamber 38 of the metering valve as shown in FIG. 2. The spring 48 through engagement with the spring guide biases the valve stem 26 toward the resting position. It will be appreciated by those skilled in the art that any suitable means for biasing the valve stem 26 into the resting position, e.g. coil compression spring or a spring appropriately mounted external to the interior chamber, may be used in connection with metering valves according to the present invention. The spring guide may be an integral part of the valve stem and/or arranged to include a pressure filling ring as described in the U.S. Pat. No. 5,400,920, which is incorporated by reference herein.

The metering valve 14 also includes at least two annular gaskets, the diaphragm 20 and the metering gasket 32. The diaphragm 20 is positioned between the valve housing 18, the valve body 22 and the valve stem 26, as shown in FIG. 2. The diaphragm 20 isolates the formulation in the aerosol container 12 from the exterior of the valve by forming two fluid tight seals: 1) an annular seal between the diaphragm 20 and the valve stem 26 where the valve stem extends out of the valve housing, and 2) a compressive planar or face seal between the diaphragm 20 and the housing 18. The latter seal may be effected either with or without a sealing bead on either the valve body 22 or the housing 18.

As shown in FIG. 2, the metering gasket 32 is included in the valve stem 26, and forms two planar face seals with the body portion of the valve stem 26. The metering gasket may be either mechanically affixed onto the valve stem, molded onto the valve stem, or the valve stem may be manufactured using, for example, a two shot or co-molding process in which the valve stem and metering gasket are co-molded so that a strong bond (mechanical and/or chemical) can be achieved between the underlying portion of the valve stem and the metering gasket. As will be described in more detail below, the metering gasket 32 transiently isolates the formulation in a metering chamber 34 (which is formed during actuation) from the aerosol container 12 (as can be best seen in FIG. 4) and thus provides a means for terminating the flow of formulation from the aerosol container 12 to the metering chamber 34 during actuation of the valve stem 26.

Figure 3:
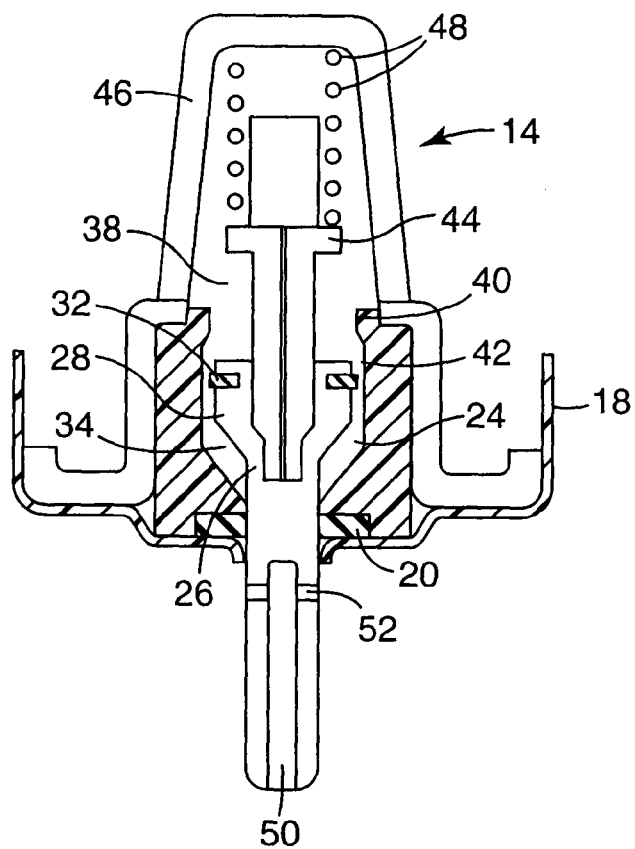
FIG. 3 is an enlarged cross-sectional view of the aerosol metering valve shown in FIG. 2 during the filling stage of valve stem actuation.
Figure 4:
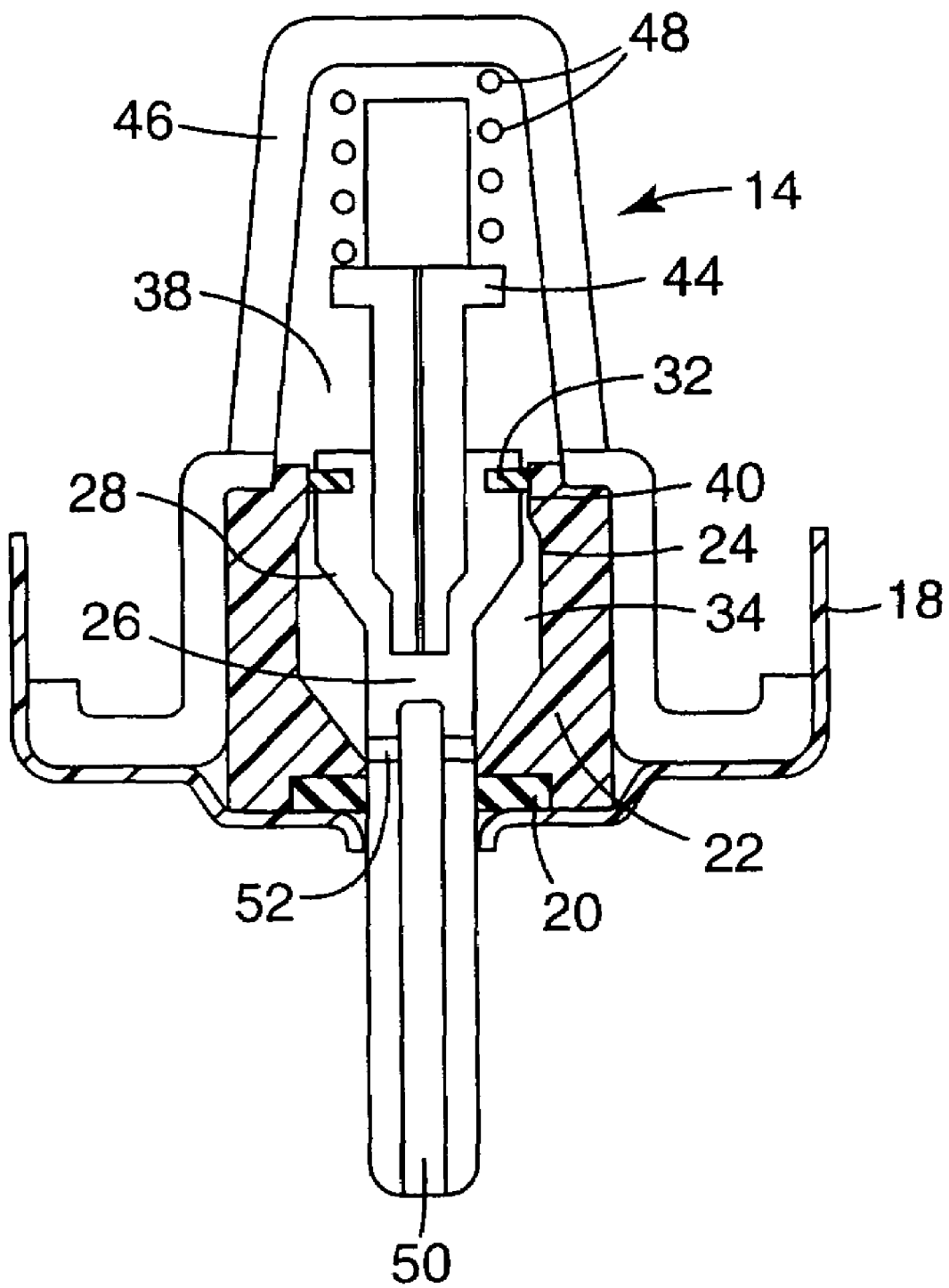
FIG. 4 is an enlarged cross-sectional view of the aerosol metering valve shown in FIG. 2 during the discharge stage of valve stem actuation.

Operation of the metering valve shown in FIG. 2 is illustrated in FIGS. 3 and 4. The figures illustrate the stages of operation of the metering valve 14 and the corresponding relative positions of the valve components as a patient actuates the valve stem 26, thereby releasing a dose of aerosol formulation. FIG. 3 shows the metering valve 14 in the filling stage and FIG. 4 shows the metering valve 14 in the discharge stage.

As can be seen in FIG. 3 during the filling stage of actuation, the valve stem 26 has been displaced inwardly into the interior chamber 38 against the compressive force of the spring 48. As the valve stem 26 is displaced inwardly, the proximal end of the stem portion of the valve stem 26 enters the valve housing 18. As a result, a metering chamber 34 is formed between the interior surface of the valve body 24 and the metering surface 28 of the valve stem 26. The volume of the metering chamber 34 increases as the valve stem is displaced until it reaches its filled-volume at the end of the filling stage.

Aerosol formulation enters the filling volume of the metering chamber 34 in the following manner. Formulation from the aerosol container 12 passes through the one or more inlets and into the interior chamber 38 of the metering valve. From the interior chamber 38, the formulation passes between the spring guide 44 and the metering gasket 32. Formulation flows around the proximal end of the valve stem 26 through a flow channel 42 between the valve stem 26 and the interior surface of the valve body 24 and enters the expanding metering chamber 34. The spring guide may be provided with cut-away portions or openings to improve flow and/or access to the metering chamber.

Thus, as the valve stem 26 is moved from the resting position shown in FIG. 2 to the filling stage shown in FIG. 3, aerosol formulation passes from the aerosol container 12 to the metering chamber 34 immediately upon actuation of the valve stem 26. Formulation continues to fill the metering chamber 34 until the metering valve 14 reaches the filled stage (not illustrated). As will be described in more detail below, the flow of formulation into the metering chamber 34 may be affected by the angle described by the metering surface of the valve stem 28 with respect to the central longitudinal axis of the valve stem.

At the end of the filling stage, the flow channel is cut off as the metering gasket contacts the sealing surface 40 of the valve body 22. The metering gasket forms a fluid-tight, sliding annular seal with the sealing surface (as can be seen in FIG. 4). The sealing surface 40 may include one or more structures designed to limit abrasion of the metering gasket 32 as the metering gasket first contacts and then slides past the sealing surface 40. Suitable structures include but are not limited to a rounded edge, a beveled edge, and a smooth angled transition from the interior surface of the valve body 24 to the sealing surface 40.

The dimensions of the valve body 22, valve stem 26 and other valve components determine the filled-volume of the metering chamber 34 in the completely filled position.

Figure 10:
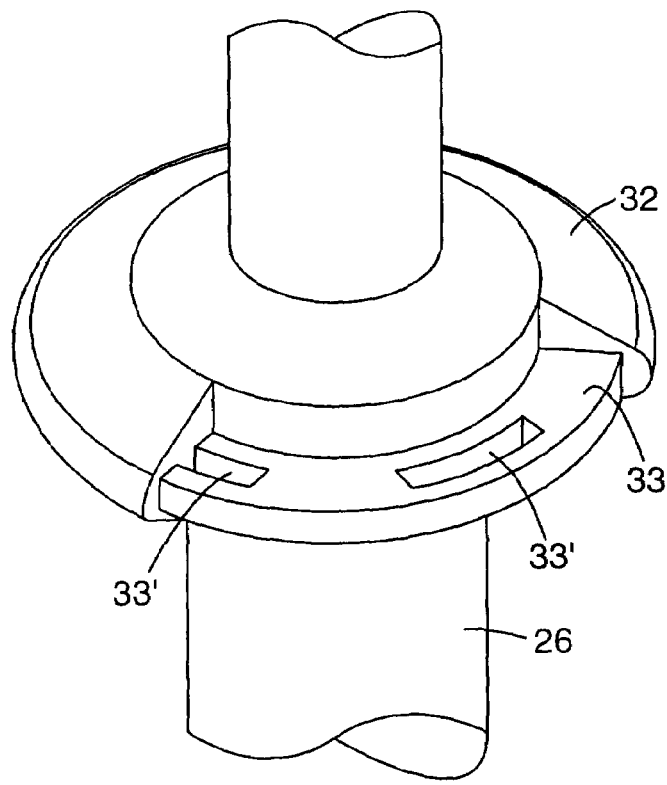
FIG. 10 is an isometric, cut-away, enlarged view of a portion, i.e. in the vicinity of the metering gasket, of a further embodiment of a valve stem for use in an aerosol metering valve according to the present invention.

FIG. 4 depicts the metering valve 14 in the discharge stage of actuation. In order to discharge the metered dose of aerosol formulation from the metering chamber 34, the valve stem 26 is further actuated to the position illustrated in FIG. 4. Those skilled in the art will realize that the distance traveled by the valve stem 26 between the start of the filled stage and FIG. 4 will result in an expansion of the metering chamber 34 without increasing the metered dose. The extra travel ensures that the metering gasket 32 is sealed against the sealing surface 40 before the one or more side holes 52 enter the metering chamber 34. As the valve stem 26 is fully actuated, the one or more side holes 52 of the discharge passageway 50 pass through the diaphragm 20 and come into fluid communication with the metering chamber 34. The fluid communication thus established allows the aerosol formulation within the metering chamber 34 to be released into the one or more side holes 52 and the formulation thus passes through the discharge passageway 50, thereby delivering the metered dose of aerosol formulation to the patient or other desired area.

During the discharge of the aerosol formulation from the metering chamber 34 as shown in FIG. 4, the metering gasket 32 continues to prevent the passage of additional bulk formulation from the aerosol container 12 to the metering chamber 34, with allowance made for the dimensional tolerances of the valve components. After the dose of aerosol formulation is discharged, the patient releases the valve stem 26, which returns to its original resting position depicted in FIG. 2 by at least the biasing action of the spring 48.

The successive stages of valve stem actuation, as exemplarily depicted in FIGS. 3 and 4, are all accomplished during the brief duration of actuation of the valve stem. Accordingly, formation, filling and emptying of the metering chamber occurs rapidly. At most, only a very small percentage of a dose of formulation resides in the metering chamber between actuations. In some embodiments, the metering chamber may not exist at all in the resting state—the residual metering volume may be zero—so that no formulation can reside in the metering chamber between actuations. Because the stages of valve stem actuation occur rapidly, the metering chamber is full of formulation only for a brief moment immediately prior to discharge of the formulation from the metering chamber.

FIGS. 5 to 7 illustrates another embodiment of a metering valve 14 in its resting position, during filling stage and discharge stage of actuation. This embodiment provides an example in which the spring guide 44 and valve stem 26 are formed as a single element. In this embodiment, the part of the metering surface 28 located adjacent to the interface between the metering surface and sealing surface has no significant portion aligned parallel or nearly parallel to the stem axis. Furthermore, the metering surface 28 is configured to have substantially the same shape as the surrounding wall of the valve body 22. Thus, in this embodiment, substantially the complete portion of the metering surface 28 of the valve stem 26 rests in contact with the interior surface of the valve body 24 when the metering valve is in the resting position (as shown in FIG. 5), thereby minimizing, if not substantially eliminating, any residual metering volume.

Also, in this embodiment the part of the sealing surface 30 located adjacent to the interface between the metering surface and sealing surface has no significant portion aligned parallel or nearly parallel to the stem axis. This facilitates free-flowing communication between the bulk formulation and formulation within the interior chamber 38, in particular in the vicinity of the body portion of the valve stem 26 and the internal chamber or cavity of the valve body 22 defined by the interior surface 24 of the valve body wall, when the metering valve is in the resting position.

During actuation of the metering valve 14 (as illustrated in FIGS. 6 and 7)—the operation of which is the same as that described for the embodiment illustrated in FIGS. 2 to 4—free flow of formulation during the filling stage (FIG. 6) into the metering chamber 34 formed upon actuation is also enhanced, as discussed in more detail below, due to the desirable configuration of the metering surface 28 and/or sealing surface 30 of the body portion of the valve stem 26.

FIG. 8 illustrates a further embodiment of a metering valve 14 in its resting position. This embodiment provides an example in which the spring guide 44 is formed of two parts, a spring guide stem 44' and a spring guide cap 44", wherein the valve stem 26 and spring guide stem are formed as a single element and the spring guide cap is formed as a separate element, which is subsequently affixed onto the spring guide stem.

In this embodiment the part of the metering surface 28 located adjacent to the interface between the metering surface and the sealing surface 30 is configured to have substantially no portion aligned parallel or nearly parallel to the stem axis. Furthermore, the metering surface 28 is configured to have essentially the same shape as the surrounding wall of the valve body 22. Thus, in this embodiment, essentially the complete portion of the metering surface 28 of the body portion of valve stem 26 rests in contact with the interior surface of the valve body 24 when the metering valve is in the resting position (as shown in FIG. 8), thereby substantially eliminating any residual metering volume. In this embodiment the part of the sealing surface 30 located adjacent to the interface between the metering surface 28 and sealing surface is also configured to have substantially no portion aligned parallel to the stem axis, in particular adjacent to the interface between the metering surface 28 and the sealing surface. This again enhances free-flowing communication between the bulk formulation and formulation within the interior chamber 38, in particular in the vicinity of the body portion of the valve stem 26 and the internal chamber or cavity of the valve body defined by the interior surface 24 of the valve body wall, when the metering valve is in the resting position As can be appreciated from FIG. 8, the metering gasket 32 of this embodiment is substantially triangular in shape. The inner surface of the metering gasket 32 is typically affixed to the respective underlying portion of the valve stem 26 as a result of a molding (e.g. molding the gasket onto a metal valve stem) or, more desirably a co-molding, manufacturing process used to produce the valve stem. As mentioned above, the use of co-molding processes allows the provision of a strong bond between the interface of the metering gasket and the underlying portion of the valve stem. To enhance bonding and/or to further ensure mechanical support and strength, the underlying portion of the valve 26 may be provided with key(s) or geometrical feature(s) 33, which facilitate or enhance mechanical anchorage of the molded or co-molded metering gasket 32. For better understanding, FIG. 9 illustrates an isometric, cut-away, enlarged view of a portion, i.e. in the vicinity of the metering gasket, of the metering valve shown in FIG. 8. As can be seen the portion of the valve stem 26 underlying the inner surface of the metering gasket 32 is provided with keys 33 in the form of a series of alternating triangular teeth, which may optionally be slightly undercut as shown. As will be appreciated the form of the key(s) may be of any suitable form, desirably a non-reentrant form for ease in manufacturing (e.g. using injection moulding tooling with an axial direction of tool half split movement), which facilitate or enhance anchorage of the metering gasket. Suitable forms include L-shaped extensions, desirably alternatively up and down, T-shaped extensions, an annular flange or as exemplified in FIG. 10 an annular flange 33 provided with holes or elongated perforations 33'.

During actuation of the metering valve 14 (not illustrated) shown in FIG. 8—the operation of which is the same as that described for the embodiment illustrated in FIGS. 2 to 4—free flow of formulation during the filling stage into the metering chamber 34 formed upon actuation is enhanced, as discussed in more detail below, due to the desirable configuration of the metering surface 28 and/or sealing surface 30 of the body portion of the valve stem 26.

As mentioned above, the configurations of the valve body 22, valve stem 26 and in some cases other valve components influence free flow of formulation and the presence of residual metering volume, when the metering valve is in its resting position as well as the flow of formulation into the metering chamber 24 when the valve stem is actuated.

For example, when the metering portion (a portion that, in part, bounds the metering chamber formed upon actuation) of the valve body is configured to substantially conform to the metering surface of the valve stem, when the metering valve is in its resting position, the presence of residual metering volume is minimized. Under the term "metering portion of the valve body is configured to substantially conform to the metering surface of the valve stem", it is desirably understood that a significant portion (e.g. $\geq 85\%$) of the metering surface of the valve stem rests in contact with the interior surface of the valve body when the metering valve is in the resting position. The residual metering volume may be further minimized, by configuring the metering portion of the valve body to essentially conform or to conform to the metering surface of the valve stem when the valve is at rest. Under the term "metering portion of the valve body is configured to essentially conform or to conform to the metering surface of the valve stem", it is desirably understood that substantially the complete portion (e.g. $\geq 90\%$) or essentially the complete portion (e.g. $\geq 95\%$ or more desirably $\geq 97.5\%$), respectively, of the metering surface of the valve stem rests in contact with the interior surface of the valve body when the metering valve is in the resting position.

As described above, free flowing of formulation in the valve in its rest position may be further desirably influenced, by configuring the metering surface of the body portion of the valve stem, such that no significant portion (e.g. $\leq 5\%$ or more desirably $\leq 2.5\%$), more suitably no substantial portion (e.g. $\leq 2\%$ or more desirably $\leq 1\%$), or most suitably no portion of the metering surface adjacent to the interface between the metering surface and the sealing surface of the body portion of the valve body is aligned parallel or nearly parallel to the stem axis (i.e., with a very small angle $\theta$, e.g., 0° or 1°). Also, free-flowing communication between the bulk formulation and formulation within the interior chamber, in particular in the vicinity of the body portion of the valve stem and the internal chamber or cavity of the valve body defined by the interior surface of the valve body wall, when the metering valve is in the resting position may be enhanced by certain configurations of the sealing surface of the body portion of the valve stem. In particular, it may be desirable to configure the sealing surface of the body portion of the valve stem, such that no significant portion (e.g. $\leq 5\%$ or more desirably $\leq 2.5\%$), more suitably no substantial portion (e.g. $\leq 2\%$ or more desirably $\leq 1\%$), or most suitably no portion of the sealing surface adjacent to the interface between the metering surface and the sealing surface of the body portion of the valve body is aligned parallel or nearly parallel to the stem axis.

Figure 11:
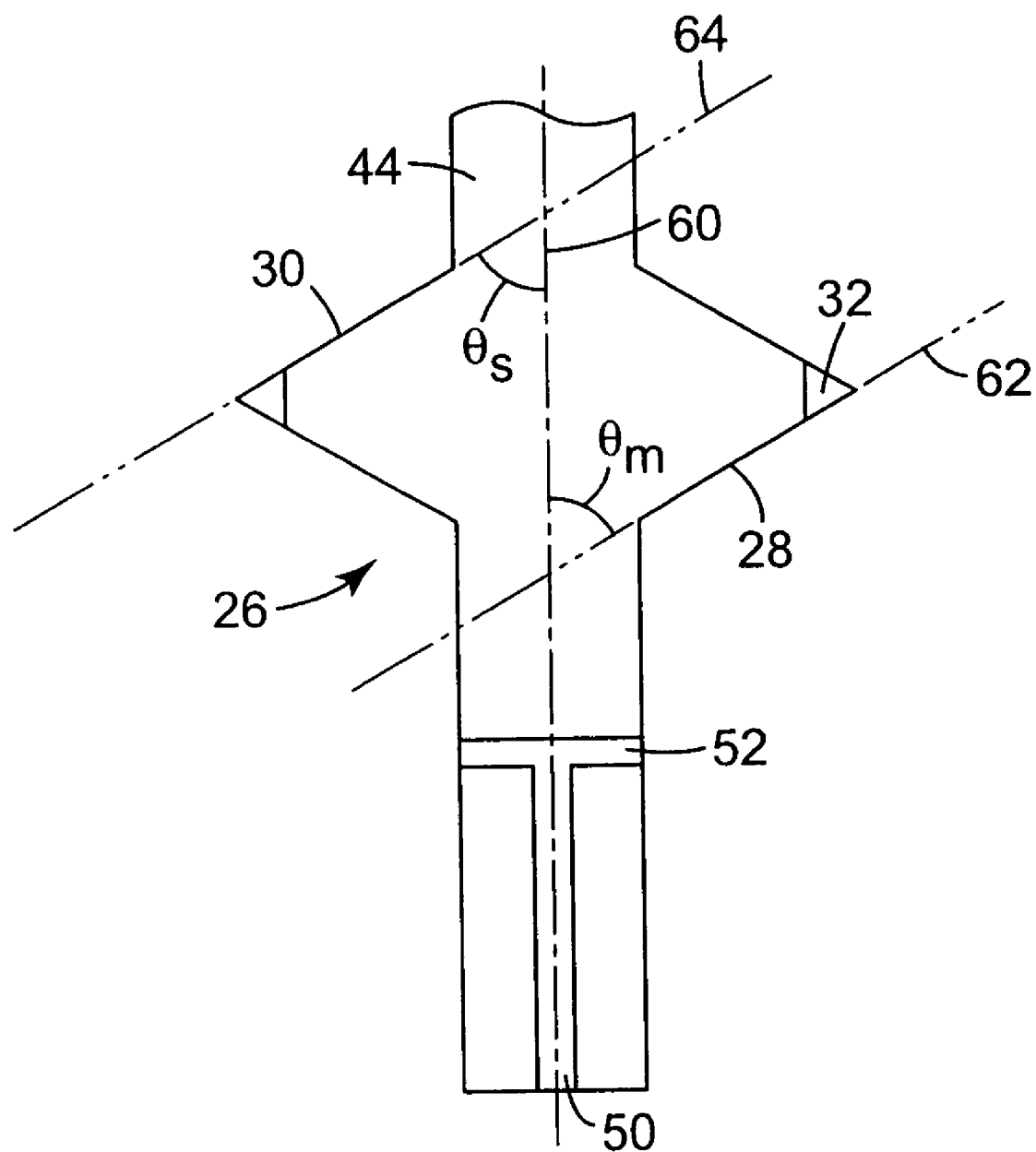
FIG. 11 is an enlarged cross-sectional view of one embodiment of a valve stem according to the present invention.
Figure 13:
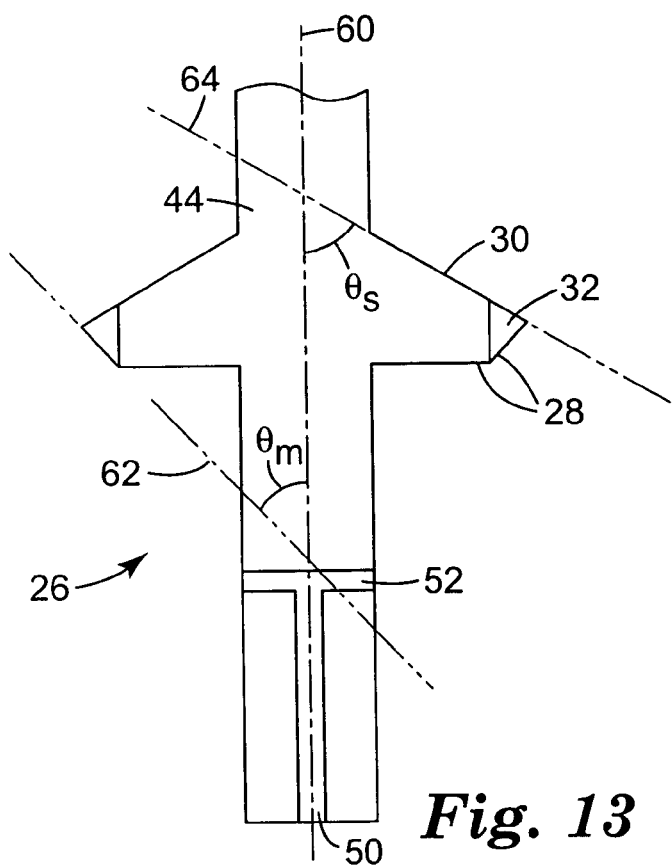
FIG. 13 is an enlarged cross-sectional view of another alternative embodiment of a valve stem according to the present invention.

As mentioned above, the flow of formulation into the metering chamber during actuation may be affected by the angle described by the metering surface of the valve stem with respect to the central longitudinal axis of the valve stem. For example, the valve stem 26 may define a central longitudinal axis 60, as shown in FIG. 11. An angle $\theta_m$ may be defined by the intersection of a plane 62 tangential to a major portion of the metering surface 28 of the valve stem and the central axis 60. In some embodiments with complex geometries, angle $\theta_m$ may be defined by the intersection of the central axis 60 and a plane tangential with a minor portion of the metering surface 28, as shown in FIG. 13.

All else being equal and assuming that the valve body is configured to substantially conform to the valve stem, a larger $\theta_m$ results in a wider filling gap for a given displacement of the valve stem during actuation of the metering valve. For given sealing diameters and a given stem displacement distance to the metering point, a larger value of $\theta_m$ generally allows the valve stem and the metering valve to be shorter. The shape of the metering surface 28 shown in FIG. 13 allows the use of a particular angle $\theta_m$ in a shorter metering valve. A simpler metering surface, such as that shown in FIG. 11, may require less dimensional control in order to manufacture the valve stem and valve body that substantially conform to one another and thereby limit or eliminate residual metering volume when the metering valve is at rest.

Suitable values for angle $\theta_m$ in valve stems according to the present invention are from about 2° to about 90°. Within this range a minimum angle of about 10° is more desirable, about 20° even more desirable and about 30° most desirable. A maximum angle of about 80° is more desirable, about 70° even more desirable and about 60° most desirable.

To limit the potential of areas of restricted flow within the metering chamber and thus enhanced free flow of formulation into the metering chamber, the metering surface is desirably configured to have no significant portion (e.g. $\leq 5\%$ or more desirably $\leq 2.5\%$), more suitably no substantial portion (e.g. $\leq 2\%$ or more desirably $\leq 1\%$), or most suitably no portion thereof aligned parallel or nearly parallel to the stem axis.

Figure 5:
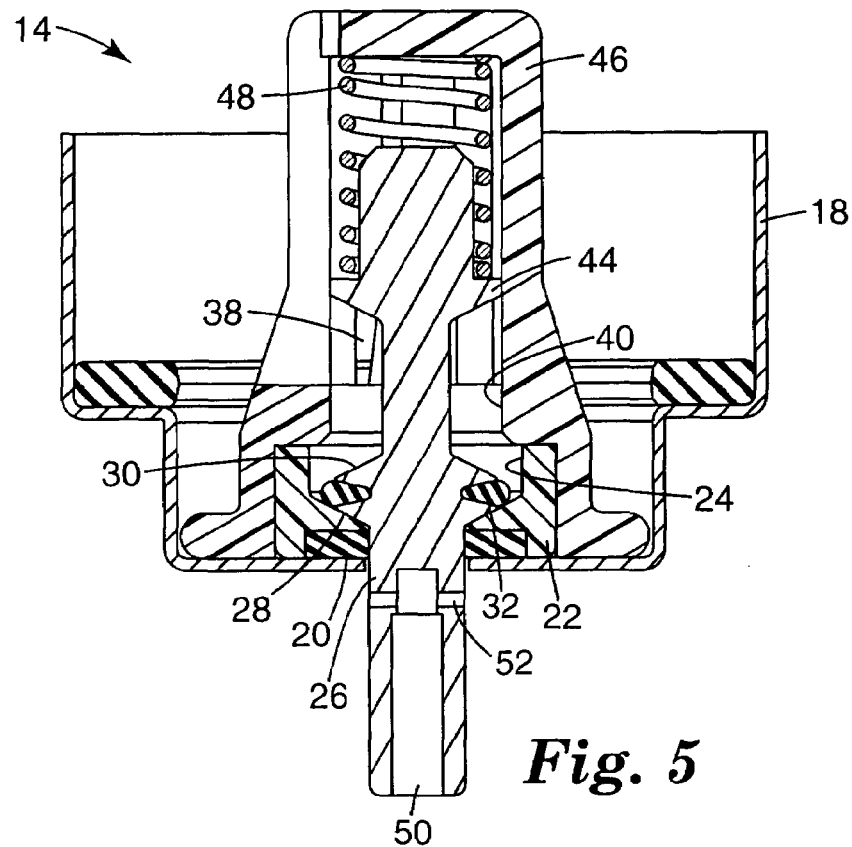
FIGS. 5 to 7 are enlarged cross-sectional views of the embodiment of an aerosol metering valve according to the present invention shown in FIG. 1 in the resting position, the filling stage and the discharge stage, respectively.
Figure 6:
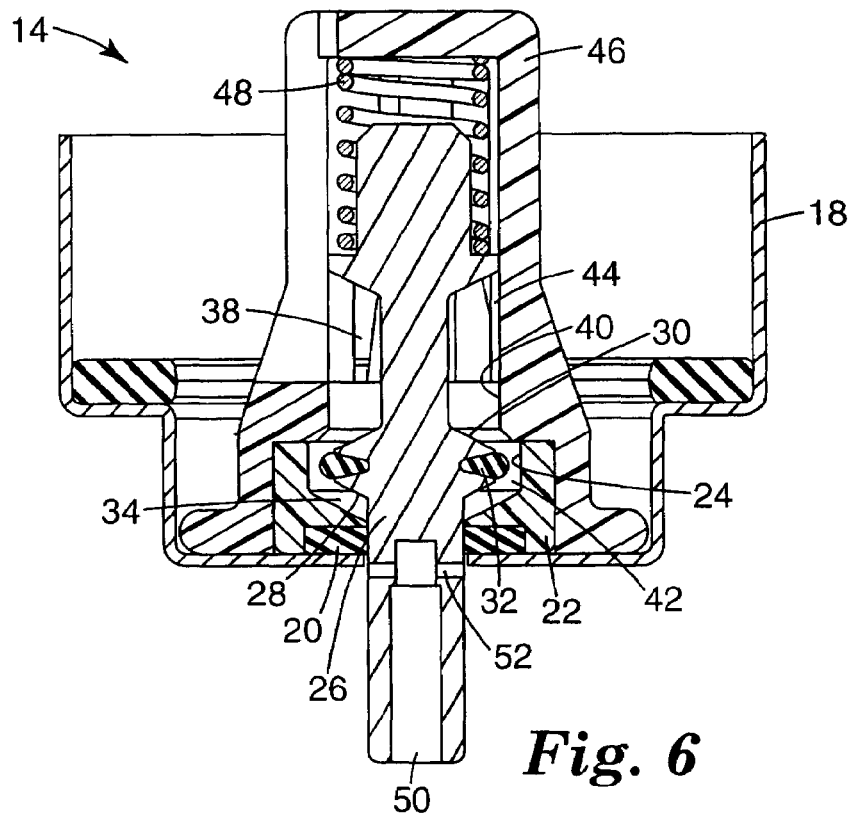
Figure 7:
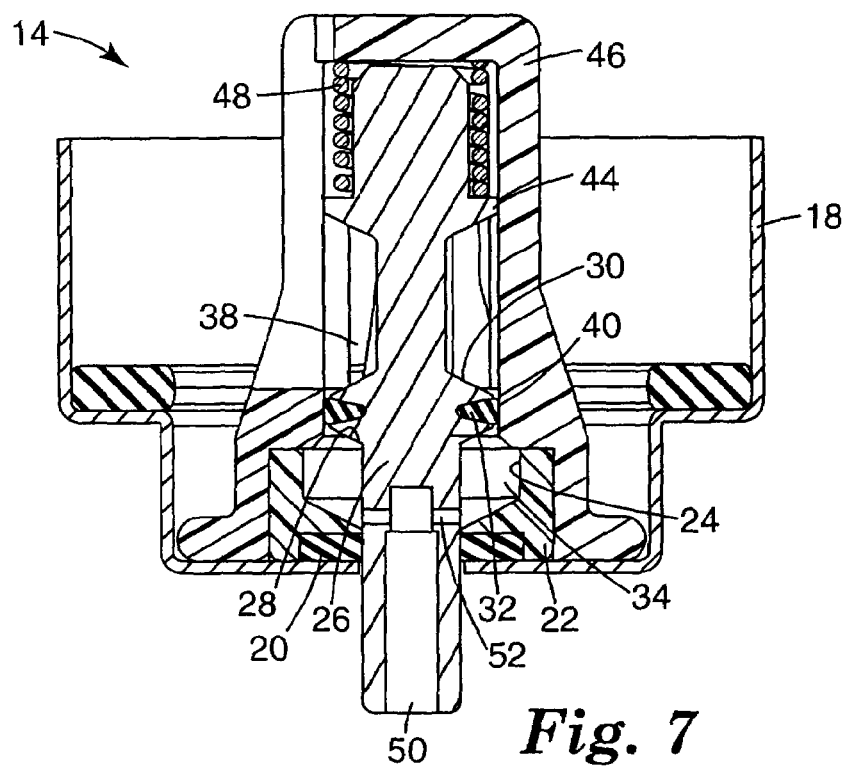
Figure 8:
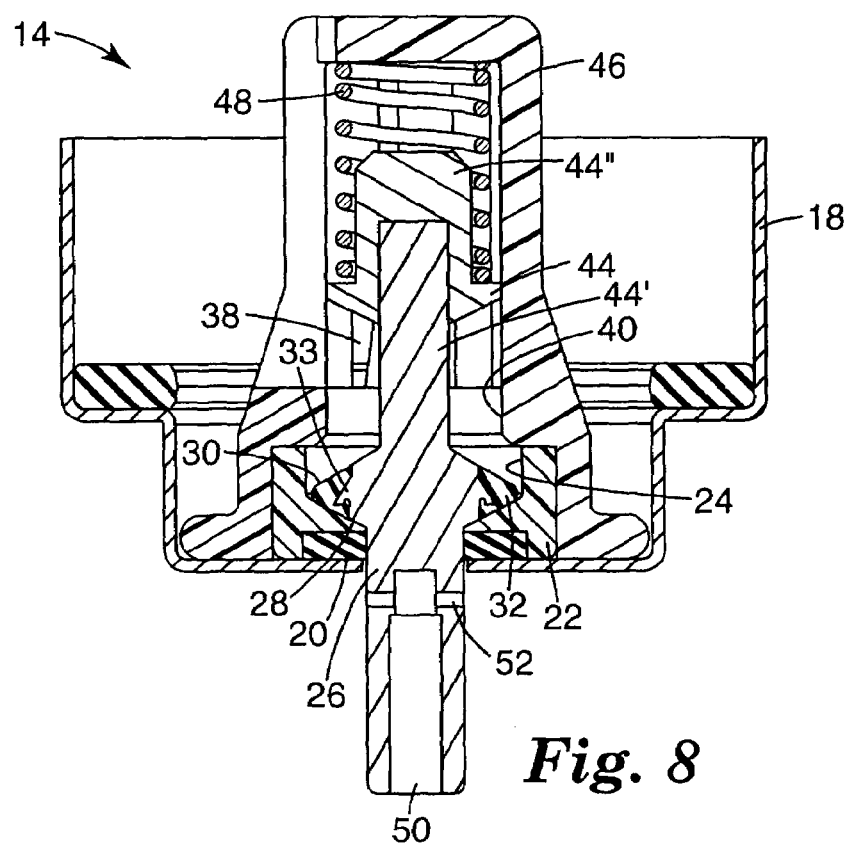
FIG. 8 is an enlarged cross-sectional view of yet another embodiment in the resting position.
Figure 9:
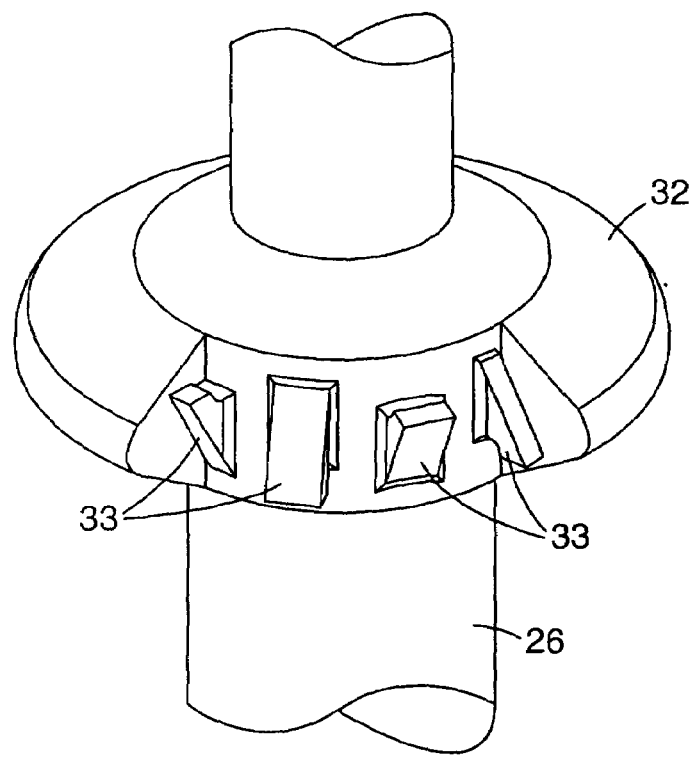
FIG. 9 is an isometric, cut-away, enlarged view of a portion, i.e. in the vicinity of the metering gasket, of the valve stem of the metering valve shown in FIG. 8.

As can be seen in the exemplary embodiments shown in FIGS. 2, 5 and 8, the body portion of the valve stem typically includes a section adjacent to the stem portion, which is aligned parallel or nearly parallel to the stem axis. This section facilitates the passage of the valve stem through the opening of the valve housing and/or the diaphragm. Because this section is adjacent to the stem portion and at the distal end of the metering chamber formed upon actuation (as can be appreciated for example in FIG. 6), a parallel or nearly parallel alignment of this section of body portion does not restrict the flow into the metering chamber.

Figure 12:
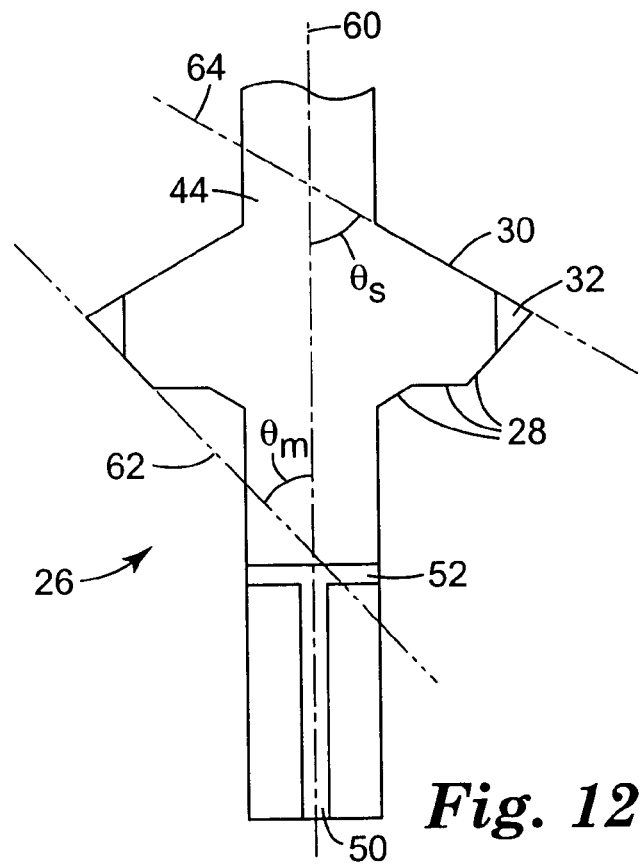
FIG. 12 is an enlarged cross-sectional view of an alternative embodiment of a valve stem according to the present invention.

As can be best seen in FIGS. 11 to 13 showing exemplary valve stems, the metering surface 28 is typically that surface of the section of the body portion located between the section of the body portion comprising the sealing surface 30 and the section of the body portion adjacent to the stem portion being aligned parallel or nearly parallel to the stem axis. The circumferential interface or boundary of the metering surface and the sealing surface, being located on the outer surface of the metering gasket, is typically understood to be the annulus of widest transverse cross section of the metering gasket. In embodiments, which in accordance to the aforesaid definition would have an interface or boundary having a portion parallel to the longitudinal axis of the stem, the interface or boundary is understood in this case to be the annulus at the distal end of the parallel portion (i.e. the end towards the stem portion). As can be appreciated from FIGS. 11 to 13, if the valve stem includes a mounted or integral spring guide 44, the sealing surface 30 ends at the interface or boundary between the surface of the body portion of the valve stem and the surface of the spring guide.

The flow of formulation into the metering chamber during actuation as well as free flow of formulation when the metering valve is at rest may also be affected by the angle described by the sealing surface of the valve stem with respect to the central longitudinal axis of the valve stem. Referring to FIG. 11, an angle $\theta_s$ may be defined by the intersection of a plane 64 tangential to a major portion of the sealing surface 30 of the valve stem and the central axis 60. In some embodiments with complex geometries, angle $\theta_s$ may be defined by the intersection of the central axis 60 and a plane tangential with a minor portion of the sealing surface 30. Typical values for angle $\theta_s$ in valve stems may be from about 30° to 90°. Within this range, a minimum angle of about 45° is more desirable and about 50° most desirable. A maximum angle of about 85° is more desirable and about 80° most desirable.

Metering valves having an angle $\theta_m$ in the ranges described may have a metering portion—a portion that, in part, bounds the metering chamber—that can generally be described as conical in shape with a cross-sectional area of the proximal portion of the cone being greater than the cross-sectional area of the distal portion of the cone. In some embodiments, the transverse cross-sectional area of the valve stem body at the metering and sealing surface interface may be about 4% greater than the transverse cross-sectional area of the distal end (i.e. towards the stem portion of the valve stem) of the valve stem body. In other embodiments, the transverse cross-sectional area of the valve stem body at the metering and sealing surface interface may be at least about 20% greater than the transverse cross-sectional area of the distal end of the valve stem body. In still other embodiments, the transverse cross-sectional area of the valve stem body at the metering and sealing surface interface may be at least about 60% greater than the transverse cross-sectional area of the distal end of the valve stem body.

In certain embodiments having a generally conical metering portion, the interior surface of the valve body maintains a generally conical form from the diaphragm to the valve body sealing surface.

The metering surface 28 of the valve stem 26 may be of any suitable configuration and still define the plane 62 used to define angle $\theta_m$. For example, in a valve stem having relatively simple geometry, such as the valve stem shown in FIG. 11, a majority of the metering surface 28 may define the plane 62 used to define angle $\theta_m$. Alternatively, the metering surface 28 may be irregular, such as is shown in FIGS. 12 and 13, and only a portion of the metering surface may be used to define the plane 62. Additionally, irregularities in the metering surface 28 may be non-geometrical and still provide a suitable configuration for valve stem 26 according to the present invention.

Thus, the particular geometry of the metering surface 28 is not critical so long as (1) angle $\theta_m$ can be defined as described herein, (2) the interior surface 24 of the valve body 22 is configured to substantially conform to the geometry of the metering surface 28. These factors contribute to limiting or eliminating residual metering volume when the metering valve is at rest and facilitate the reduction of restriction of the flow of formulation to the metering chamber. Furthermore, it may be advantageous for limiting or eliminating residual metering volume that no significant portion of the metering surface and/or the sealing surface adjacent to the interface between the metering surface and the sealing surface is aligned parallel or nearly parallel to the stem axis. The metering surface may be configured to have no significant portion aligned parallel or nearly parallel to the stem axis. This may contribute to limiting the formation of areas of restricted flow within the metering chamber and thus restriction on the free flow of formulation into the metering chamber even though the interior surface 24 of the valve body 22 substantially conforms to the geometry of the metering surface 28.

Simple geometries for the metering surface 28 and the interior surface 24 of the valve body may provide certain manufacturing advantages. For example, valve stems having complete 360° rotational symmetry require no rotational alignment during valve assembly. Simple shapes such as cones might also confer certain performance advantages. For example, simple shapes may reduce problems with deposition of drug or with formulation flow discontinuities at angular edges. However, more complex geometries also are suitable for valve stems 26 according to the present invention. For example, some embodiments may include hemispherical or other curved configurations. Other embodiments may include valve stems having multiple angles, such as those shown in FIGS. 12 and 13.

The embodiments described above are provided in the context of metering valves having a displaceable valve stem surrounded by a valve body. However, one also may design a metering valve in which the displaceable valve stem surrounds the valve body. Such an embodiment is shown in FIGS. 14–16. FIG. 14 shows the embodiment in the resting stage, FIG. 15 shows the same embodiment in the filling stage, and FIG. 16 shows the same embodiment in the discharge stage.

The metering valve 114 of FIG. 14 includes a housing 118 that serves to house the various components of the metering valve 114. The top portion of the housing 118 attaches to the aerosol container as shown with respect to an alternative embodiment in FIG. 1. A valve body 122 is seated within the valve housing 118 and in turn provides a housing for a valve stem 126.

The metering valve 114 includes a metering body 124 that, together with the valve body 122, defines an interior chamber 138 that is partially occupied by a portion of the valve stem 126. At least one inlet (not shown) provides open and unrestricted fluid communication between the interior chamber 138 and the bulk formulation stored in the aerosol container.

In the embodiment shown in FIGS. 14–16, the metering body includes a stem portion 123 that generally defines a central axis 160. The stem portion 123 of the metering body 124 includes an inlet recess 112, a sealing surface 113, a metering surface 116, and a discharge gasket 117. The discharge gasket 117 forms a sliding seal with the interior surface of the valve stem 130 and isolates the interior chamber 138 from the exterior of the valve when the metering valve is in the resting position.

A portion of the valve stem 126 resides within the housing 118 throughout actuation. Another portion of the valve stem 126 resides outside the valve housing 118 when the valve stem 126 is in the resting position shown in FIG. 14. During actuation of the valve stem 126, a portion of the valve stem 126 that resides outside the housing 118 will be displaced inwardly with respect to the metering valve 114 so that it will be transiently positioned inside the valve housing 118.

Figure 14:
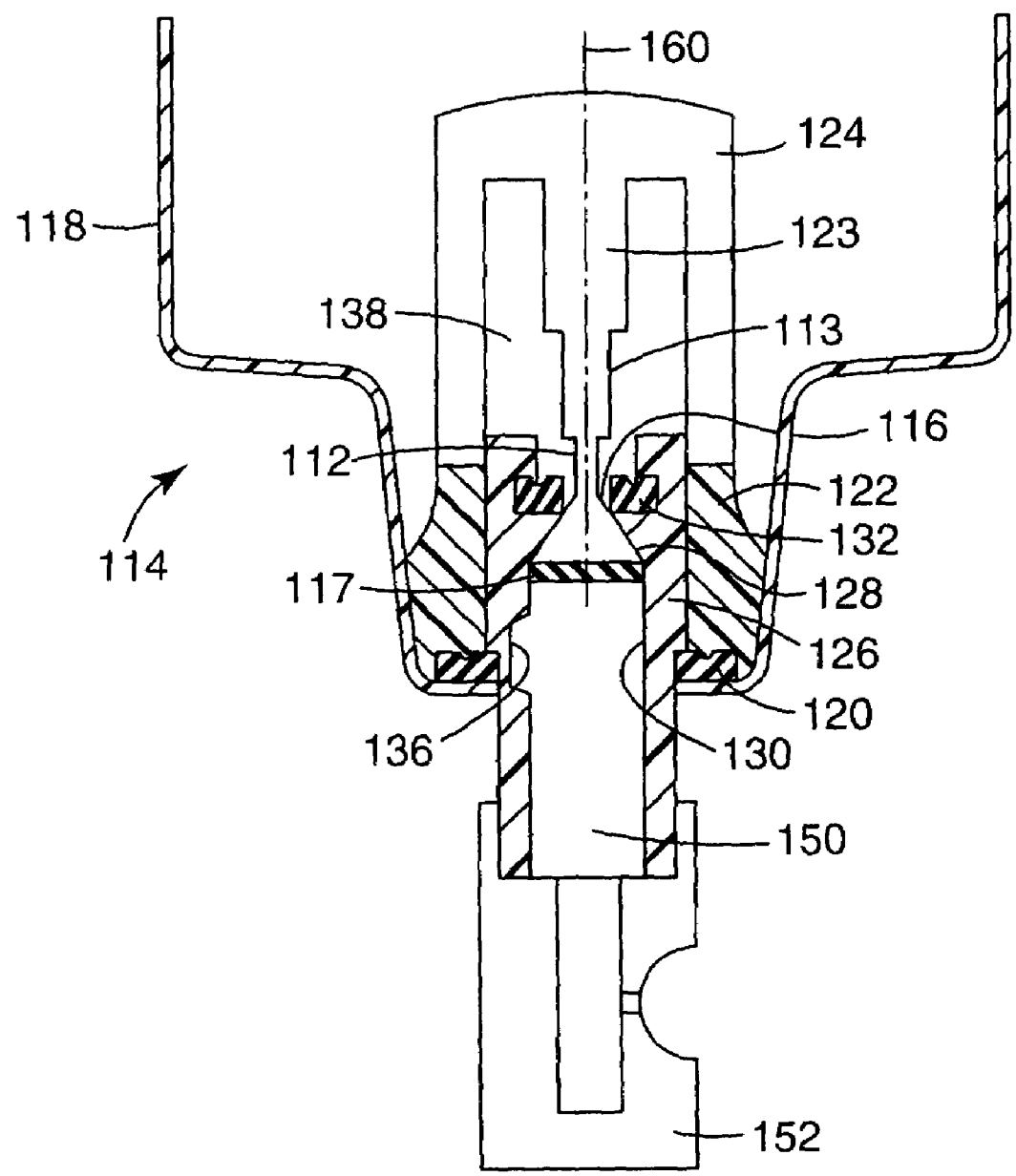
FIGS. 14 to 16 are enlarged cross-sectional views of an alternative embodiment of a metering valve according to the present invention in the resting position, the filling stage and the discharge stage, respectively.
Figure 15:
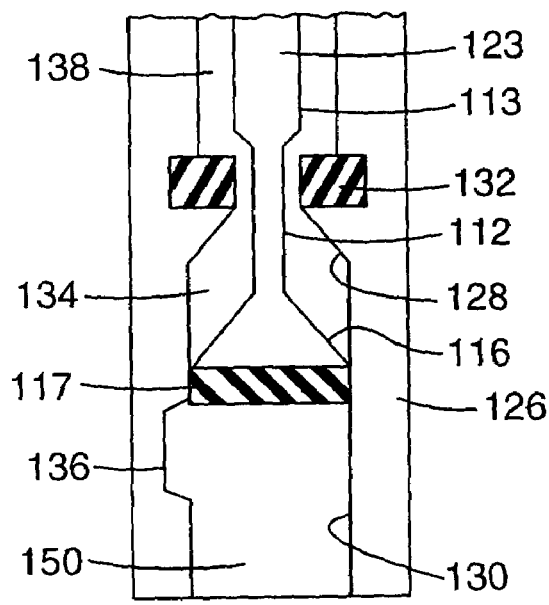
Figure 16:
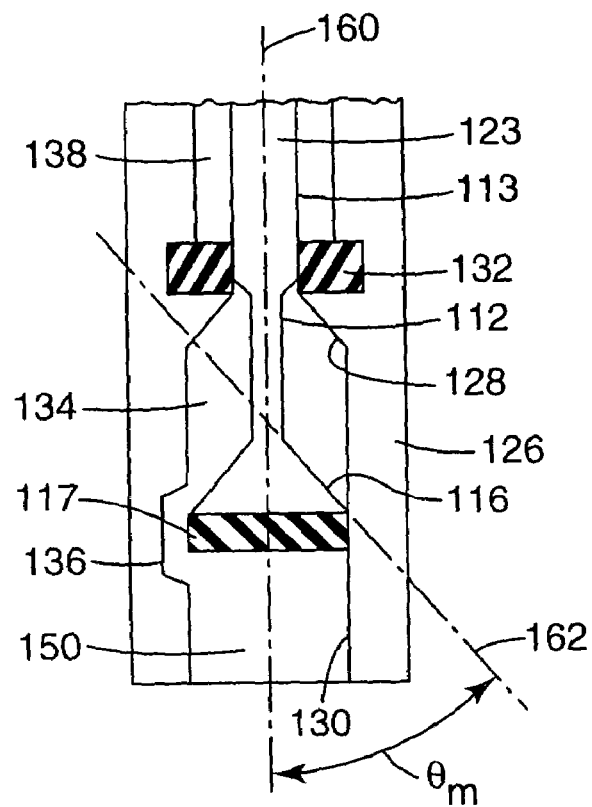

The valve stem 126 of the metering valve 114 shown in FIGS. 14–16 includes a metering gasket 132. The metering gasket 132 forms a planar face seal with the valve stem 126 and is positioned so that it can form a sliding annular seal with the sealing surface 113 of the stem portion 123 of the metering body 124. The valve stem 126 also includes a metering surface 128, a discharge recess 136, and a discharge passageway 150. The discharge passageway 150 may be in fluid communication with a discharge piece 152.

FIG. 15 shows the metering valve of FIG. 14 in the filling stage of actuation. The valve stem 126 is shown partially actuated—it has been displaced inward with respect to the stem portion 123 of the metering body 124 and, therefore, also with respect to the entire metering valve. Thus, the valve stem metering surface 128 has been drawn away from the metering surface 116 of the metering body. The resulting space defines, in part, the metering chamber 134. Formulation is permitted to flow from the interior chamber 138, through the passage formed between the metering gasket 132 and the inlet recess 112, and into the metering chamber 134.

In operation, the valve stem 126 is further actuated to the filled stage (not shown). In the filled stage, the metering gasket 132 eventually contacts the sealing surface 113 and forms a fluid-tight sliding seal. This seal isolates the metering chamber 134 from the interior chamber 138 and stops the flow of formulation into the metering chamber 134.

FIG. 16 shows the valve stem 126 actuated to the discharge stage. The valve stem 126 is shown actuated sufficiently so that the discharge recess 136 allows metered formulation to flow from the metering chamber 134, around the discharge gasket 117, and into the discharge passageway 150, from which the metered dose of formulation may be delivered to a patient. The metering gasket 132 maintains the sliding seal with the sealing surface 113, thereby continuing to isolate formulation in the interior chamber 138 from the exterior of the valve.

FIG. 16 also shows the determination of angle $\theta_m$ in the illustrated embodiment. As with the embodiments shown above, angle $\theta_m$ is defined by the central axis (shown as 160 in FIG. 16) and a plane (shown as 162 in FIG. 16) tangential to at least a portion of the metering surface. In this embodiment, the plane used to define angle $\theta_m$ is tangential to at least a portion of the metering surface 116 of the stem portion of the metering body 123.

Because angle $\theta_m$ is defined, in part, by a plane tangential to a portion of the metering surface 116 of the stem portion of the metering body 123, the distal portion of the metering body—the portion near the discharge gasket 117—will have a transverse cross-sectional area greater than the transverse cross-sectional area of the proximal portion of the metering body 123—that portion near the inlet recess 112. In some embodiments, the transverse cross-sectional area of the distal end of the metering body may be about 4% greater than the transverse cross-sectional area of the proximal end of the metering body. In other embodiments, the transverse cross-sectional area of the distal end of the metering body may be at least about 20% greater than the transverse cross-sectional area of the proximal end of the metering body. In still other embodiments, the transverse cross-sectional area of the distal end of the metering body may be at least about 60% greater than the transverse cross-sectional area of the proximal end of the metering body.

As with the embodiments described above, the metering surface 116 of the stem portion of the metering body 123 may substantially conform to the shape and dimensions of the metering surface of the valve stem 128. Thus, a metering valve employing this design may limit or even eliminate residual metering volume between the metering body metering surface 116 and the valve stem metering surface 128 when the metering valve is in the resting position.

The design of the metering surfaces according to the present invention may contribute, along with other aspects of metering valve or valve stem design, to improve the flow of formulation through the metering valve during actuation. Accordingly, the designs of the present invention may be used in conjunction with general metering valve designs other than those explicitly shown in the Figures. Such alternative metering valve designs may include one or more additional features of the valve stem, valve body, or any other portion of the metering valve designed to improve performance of the metering valve. Such additional design features may improve metering valve performance by improving performance parameters including but not limited to formulation flow from the aerosol container to the metering chamber during actuation and consistency of formulation metering.

For embodiments including a co-molded metering gasket, the non-metering-gasket portion of the valve stem (including the stem portion, most of the body portion and possibly the spring guide or a portion thereof), termed as the elongate stem element in the following, is desirably made of a material comprising a polymer. Suitable polymers include acetal, nylon, polyester (PE), in particular polybutylene terephthalate (PBT), polymethylpentene (PMP), polyphenylenesulfide (PPS), polyaryletherketones (PAEKs), thermotropic liquid crystalline polymers (LCPs), polypropylene, high density polypropylene, ethylene-tetrafluoroethylene copolymer (ETFE), poly-vinylidene difluoride (PVDF) and mixtures thereof. The material may include typical fillers, such as fibers (e.g. glass, mineral or carbon fibers), minerals (e.g. $CaCO_3$), graphite or carbon, which may enhance structural robustness. PPS- and PBT-containing materials desirably incorporate fillers, e.g. made of glassfiber, while the other polymer-containing materials are desirably free of fillers. For the provision of valve stems showing desirable resistance to mechanical and/or thermal stress or deformation, the polymer is desirably selected from the group consisting of polyaryletherketones, such as polyetheretherketone, thermotropic liquid crystalline polymers, polymethylpentene, polyphenylene sulfide and mixtures thereof.

The metering gasket is typically elastomeric and may be made of a material comprising a thermoplastic elastomer or a thermoset elastomer.

Various classes of suitable thermoplastic elastomers include polyester rubbers, polyurethane rubbers, ethylene vinyl acetate rubber, styrene butadiene rubber, copolyester thermoplastic elastomers, copolyester ether thermoplastic elastomers, olefinic thermoplastic elastomers, polyester amide thermoplastic elastomers, polyether amide thermoplastic elastomers, copolyamide thermoplastic elastomers and mixtures thereof. Examples of olefinic thermoplastic elastomers are described in WO 92/11190, which is incorporated herein by reference, and include block copolymers of ethylene with monomers selected from but-1-ene, hex-1-ene and oct-1-ene. Other examples of suitable olefinic thermoplastic elastomers are described in WO 99/20664, which is incorporated herein by reference, and in U.S. Pat. No. 5,703,187 (Dow). Styrene-ethylene-butadiene-styrene copolymers and blends, such as those described in WO 93/22221 and WO 95/03984, both of which are incorporated herein by reference, as well as styrene-ethylene-propylene-styrene copolymers are suitable thermoplastic elastomers. An example of a polyether amide thermoplastic elastomer is PEBAX (Atofina), which is a polyether-block-co-polyamide. Compositions comprising a mixture of inter-dispersed relative hard and relative soft domains may also be employed as suitable thermoplastic elastomers. Examples of such mixture compositions include SANTOPRENE (Advanced Elastomer Systems) which has thermoset EPDM dispersed in a polyolefin matrix or ESTANE (Noveon) which is a polymer of segmented polyester urethanes with a mixture of crystalline and rubbery nanophases. Other mixtures include olefinic thermoplastic/rubber blends and polyvinyl chloride/rubber blends. Other possibilities include single-phase melt-processable rubbers and ionomers.

Preferred thermoset elastomers include thermoset ethylene-propylene-diene terpolymer (EPDM), acrylonitrile-butadiene copolymer (Nitrile rubber), isobutylene-isoprene copolymer (Butyl rubber), halogenated isobutylene-isoprene copolymer (in particular Chlorobutyl rubber and Bromobutyl rubber), polychloroprene (Neoprene), and mixtures thereof, with EPDM, nitrile rubber and butyl rubber being more preferred, EPDM and nitrile rubber even more preferred and EPDM most preferred.

Combinations of co-molded metering gaskets made of materials comprising thermoset EPDM, nitrile rubber, butyl rubber, chlorobutyl rubber, bromobutyl rubber and/or neoprene, in particular EPDM, with elongate stem elements made of materials comprising a PAEK, LCP, PPS and/or PMP polymer provide valve stems having particularly advantageous properties in regard to mechanical and/or chemical stress resistance in dispensing valves (e.g. metered dose dispensing valves) for delivery of medicinal aerosol formulations. It is to be understood that each of the possible 24 metering gasket/elongate stem element material combinations is individually disclosed here. Valve stems comprising elongate stem elements made of materials comprising PAEK, more particularly polyetheretherketone, and co-molded metering gasket(s) made of materials comprising thermoset EPDM show superior structural and/or chemical properties towards medicinal aerosol formulations, in particular medicinal aerosol formulations comprising liquefied propellant HFA 134a and/or HFA 227, more particularly such formulations comprising additionally ethanol.

The valve stem may be manufactured by an over-molding or an under-molding process.

The former method comprises the steps of:
a) providing a first mold shape;
b) molding a first material comprising a polymer to form the elongate stem element;
c) providing a second mold shape containing at least in part the elongate stem element; and
d) molding a second material to form the metering gasket, such that the metering gasket is co-molded with at least a portion of the elongate stem element.

The second, under-molding, method comprises the steps of:
a) providing a second mold shape;
b) molding a second material to form the metering gasket;
c) providing a first mold shape underlying at least in part the metering gasket; and
d) molding a first material comprising a polymer to form the elongate stem element having the metering gasktet co-molded with at least a portion of said elongate stem element.

For the sake of consistency in the two alternative methods, the wording "first" mold shape and "first" material are used here in connection with steps relating to the molding of the elongate stem element, while the wording "second" mold shape and "second" material are used in connection with steps relating to molding of the metering gasket, regardless of the sequential order of the process steps. For molding of the elongate stem element and/or molding of the metering gasket the preferred method of molding is injection molding.

It will be appreciated by those skilled in the art that respective mold shapes will be provided as to allow the provision of the particular form of elongate stem element and metering gasket needed for the use of the valve stem in the particular dispensing valve. The method may involve a molded component being removed from its mold and then positioned appropriately in another mold form for the molding of the other component. Alternatively the method may involve a single, repositionable or form-changeable mold, in which upon molding of a component, the mold is re-positioned or changed to provide the appropriate form shape for molding of the other component.

For valve stems which include a metering gasket made of a material comprising a thermoset elastomer, the material used in the molding steps, more particularly injection molding steps, for forming seal elements ("the second material") desirably comprises a thermosettable elastomer. A thermosettable elastomer is understood here to mean a material (more particularly an injection moldable material) comprising a polymer molecule having at least one double bond, in particular polymer molecules having alkene groups, more particularly pendant alkene groups, which provides sites across which cross-links can be formed upon a curing process allowing the provision of a thermoset elastomer.

For example, thermosettable elastomers used to provide thermoset EPDM (ethylene-propylene-diene terpolymer) and nitrile rubber (an acrylonitrile-butadiene copolymer) typically comprise a polymerized diene, which provides alkene groups in the polymer for cross-linking. Butyl rubber is typically made from a polymer comprising polyisobutene with a minor proportion of isoprene to provide alkene groups for cross-linking, while halogenated butyl rubber, e.g. CIIR and BIIR, is typically made by halogenation of the respective polymer prior to curing. Halogenation does not result in a loss of unsaturation, and cross-linking is typically achieved using magnesium oxide and/or zinc oxide, preferably zinc oxide, resulting in the elimination of the respective metal halide. Similarly Neoprene is typically cross-linked via the elimination of metal chloride from polychloroprene using magnesium oxide and/or zinc oxide optionally with an alkyl diamine.

In the methods of manufacturing, subsequent to the step of molding (more particular injection molding) a second material comprising a thermosettable elastomer, the methods would include a step of curing said second material. The curing step, which is typically performed directly after the step of molding of the second material, may be performed at appropriate time after said molding and prior to remove the final mold shape in the process.

The curing process is desirably performed such that at least a majority of the cross-link bonds is formed. Processes for cross-linking are well known and two common types include sulfur-curing, which typically involves sulfur donor molecules to provide polysulfide bridges, and peroxide curing, in which peroxide molecules provide a source of free radicals allowing alkene or pendant alkene groups to form a bridge. Peroxide curing is typically the preferred method of curing, in order to provide materials from which a minimum of harmful extractables could potentially be leached. In peroxide curing to provide a halogentated butyl rubber, such as CIIR and BIIR, a co-vulcanizing agent, such as N,N'-m-phenylene-dimaleimide, is often used to achieve adequate cross-linking. Curing processes typically also involve thermal treating, e.g. heating between 110 and 200° C. for a minute or more, allowing at least a majority of the cross-link-bonds to be formed. The optimal curing conditions, curing agents, etc. depend on the particular thermosettable elastomer being molded and possibly also on the overall dimensions, size and/or form of the particular metering gasket being molded. In regard to process efficiency, it may be desirable to use higher temperatures over shorter times to achieve rapid turnover through the molding tools.

In both methods after the curing step and the removing of the final mold shape, it may be desirable to perform an additional thermal treatment step, for example to substantially complete cross-linking and/or to optimize physical properties of the thus formed metering gasket. This thermal treatment step may involve heating between 110 and 200° C. for typically a longer time period than the curing step, e.g. over a time period of 0.5 to 24 hours.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An aerosol metering valve comprising:
   (a) a valve stem that generally defines a longitudinal axis and comprises:
      (1) a body portion comprising a metering surface, wherein the longitudinal axis and a plane tangential to at least a portion of the metering surface define an angle from about 2° to about 90°, and
      (2) a stem portion comprising a discharge passageway, and;
      (3) a metering gasket;
   (b) a valve body comprising:
      (1) a body wall that comprises a sealing portion,
      (2) an internal chamber defined at least in part by the body wall and comprising a metering portion configured to substantially conform to the metering surface of the valve stem, and
   (c) a diaphragm having walls that define an aperture in slidable, sealing engagement with the stem portion of the valve stem; and
   wherein the metering gasket is configured to be able to form a transient, substantially fluid-tight seal between the valve stem and the sealing portion of the body wall.

2. An aerosol metering valve according to claim 1, wherein the body portion of the valve stem comprises a sealing surface adjacent to the metering surface and distant to the stem portion of the valve stem and wherein said sealing surface and the metering surface form a circumferential interface on the outer surface of the metering gasket.

3. An aerosol metering valve according to claim 2, wherein no significant portion of the metering surface and/or the sealing surface of the valve stem adjacent to the interface between the metering surface and the sealing surface is aligned parallel or nearly parallel to the longitudinal axis.

4. An aerosol metering valve according to claim 2, wherein the longitudinal axis and a plane tangential to at least a portion of the sealing surface define an angle from about 30° to about 90°.

5. An aerosol metering valve according to claim 1, wherein the metering gasket is configured to be able to form a substantially fluid-tight, sliding seal with at least a portion of the sealing portion of the body wall.

6. An aerosol metering valve according to claim 1, wherein the metering surface angle is equal to or greater than about 10°.

7. An aerosol metering valve according to claim 1, wherein the metering surface angle is equal to or greater than about 20°.

8. An aerosol metering valve according to claim 1, wherein the metering surface angle is equal to or greater than about 30°.

9. An aerosol metering valve according to claim 1, wherein the metering surface angle is equal to or less than about 80°.

10. An aerosol metering valve according to claim 1, wherein the metering surface angle is equal to or less than about 70°.

11. An aerosol metering valve according to claim 1, wherein the metering surface angle is equal to or less than about 60°.

12. An aerosol metering valve according to claim 1, wherein the metering surface comprises no significant portion aligned parallel or nearly parallel to the longitudinal axis.

13. An aerosol metering valve according to claim 1, wherein the metering gasket is co-molded with at least a portion of the valve stem.

14. An aerosol metering valve according to claim 1, wherein the metering gasket is made of a material comprising a thermoplastic elastomer or a thermoset elastomer and wherein a non-metering-gasket portion of the valve stem is made of a material comprising a polymer.

15. An aerosol metering valve according to claim 14, wherein the polymer comprises acetal, nylon, polyester, polybutylene terephthalate, polymethylpentene, polyphenylenesulfide, polyaryletherketones, thermotropic liquid crystalline polymers, polypropylene, high density polypropylene, ethylene-tetrafluoroethylene copolymer, poly-vinylidene difluoride, or a mixture including any of the foregoing.

16. An aerosol metering valve according to claim 15, wherein the polymer comprises polyaryletherketones, thermotropic liquid crystalline polymers, polymethylpentene, polyphenylene sulfide, or a mixture including any of the foregoing.

17. An aerosol metering valve according to claim 14, wherein the thermoset elastomer comprises EPDM, nitrile, butyl rubber, chlorobutyl rubber, bromobutyl rubber, neoprene, or a mixture including any of the foregoing.

18. A metered dose dispensing device comprising an aerosol metering valve according to claim 1.

19. A metered dose dispensing device according to claim 18, wherein said metered dose dispensing device is a metered dose inhaler.

20. An aerosol metering valve comprising:
   (a) a valve body that comprises a diaphragm having walls that define an aperture;

(b) a metering stem that generally defines a longitudinal axis and also partially defines an interior space, the metering stem comprising a sealing portion, an inlet recess distal to the sealing portion, a metering surface distal to the inlet recess, and a discharge gasket distal to the metering surface, wherein the central axis and a plane tangential to at least a portion of the metering surface defines an angle from about 2° to about 90°;

(c) a valve stem in slidable, sealing engagement with the aperture and comprising:
  (1) a sealing portion across a portion of the interior space from the inlet recess of the metering stem; said sealing portion comprising a metering gasket configured to be able to form a transient fluid-tight seal between the valve stem and the sealing portion of the metering stem,
  (2) a metering surface configured to substantially conform to the metering surface of the metering stem,
  (3) an interior surface,
  (4) a discharge recess in a portion of the interior surface, and
  (5) a discharge passageway.

21. The aerosol metering valve according to claim 20, wherein the metering gasket is configured to be able to form a substantially fluid-tight sliding seal with at least a portion of the sealing portion of the metering stem.

22. An aerosol metering valve according to claim 20, wherein the metering surface angle is equal to or greater than about 10°.

23. An aerosol metering valve according to claim 20, wherein the metering surface angle is equal to or greater than about 20°.

24. An aerosol metering valve according to claim 20, wherein the metering surface angle is equal to or greater than about 30°.

25. An aerosol metering valve according to claim 20, wherein the metering surface angle is equal to or less than about 80°.

26. An aerosol metering valve according to claim 20, wherein the metering surface angle is equal to or less than about 70°.

27. An aerosol metering valve according to claim 20, wherein the metering surface angle is equal to or less than about 60°.

28. An aerosol metering valve according to claim 20, wherein the metering surface comprises no significant portion aligned parallel or nearly parallel to the longitudinal axis.

29. An aerosol metering valve according to claim 20, wherein the metering gasket is co-molded with at least a portion of the valve stem.

30. An aerosol metering valve according to claim 20, wherein the metering gasket is made of a material comprising a thermoplastic elastomer or a thermoset elastomer and wherein a non-metering-gasket portion of the valve stem is made of a material comprising a polymer.

31. An aerosol metering valve according to claim 30, wherein the polymer comprises acetal, nylon, polyester, polybutylene terephthalate, polymethylpentene, polyphenylenesulfide, polyaryletherketones, thermotropic liquid crystalline polymers, polypropylene, high density polypropylene, ethylene-tetrafluoroethylene copolymer, poly-vinylidene difluoride, or a mixture including any of the foregoing.

32. An aerosol metering valve according to claim 31, wherein the polymer comprises polyaryletherketones, thermotropic liquid crystalline polymers, polymethylpentene, polyphenylene sulfide, or a mixture including any of the foregoing.

33. An aerosol metering valve according to claim 30, wherein the thermoset elastomer comprises EPDM, nitrile, butyl rubber, chlorobutyl rubber, bromobutyl rubber, neoprene, or a mixture including any of the foregoing.

34. A metered dose dispensing device comprising an aerosol metering valve according to claim 20.

35. A metered dose dispensing device according to claim 34, wherein said metered dose dispensing device is a metered dose inhaler.

* * * * *